US00PP11289P

United States Patent [19]

Stravers

[11] Patent Number: Plant 11,289

[45] Date of Patent: Mar. 14, 2000

[54] GERBERA PLANT NAMED 'TERCEDI'

[75] Inventor: Lambertus Johannes Maria Stravers, NG Kudelstaart, Netherlands

[73] Assignee: Terra Nigra Holding B.V., De Kwakel, Netherlands

[21] Appl. No.: 09/048,201

[22] Filed: Mar. 26, 1998

[51] Int. Cl.[7] ..... A01H 5/00

[52] U.S. Cl. ..... Plt./357

[58] Field of Search ..... Plt./357

[56] References Cited

U.S. PATENT DOCUMENTS

P.P. 7,405 12/1990 Segers ..... Plt./357
P.P. 8,816 7/1994 Stravers ..... Plt./357

OTHER PUBLICATIONS

Huxley, Anthony, ed., The New RHS Dictionary of Gardening, vol. 2, Stockton Press, NY, p. 402, 1992.

*Primary Examiner*—Howard J. Locker
*Assistant Examiner*—Wendy A Baker

[57] ABSTRACT

A new and distinct cultivar of Gerbera plant named 'Tercedi', as illustrated and described, characterized by its semi-double type, bright yellow ray florets which are a solid yellow color throughout, yellowish green disc before flowering of the individual disc florets, very little anthocyanin coloration at the base of the peduncle and the petiole, with a plant height of 35 cm excluding flowers, and an overall flower diameter of 115 mm.

1 Drawing Sheet

BACKGROUND OF THE INVENTION

The present invention comprises a new and distinct cultivar of *Gerbera jamesonii*, referred to by the cultivar name 'Tercedi'.

'Tercedi' was originated from a hybridization program in De Kwakel, The Netherlands in 1994. The female parent was 'Tereeuw' and the male parent was the unnamed seedling 89.274 (unpatented). The female parent 'Tereeuw' differs from the present invention by its color, which contains more orange. 'Tereeuw' has been available outside Terra Nigra and is registered in the U.S.A. (U.S. Plant Pat. No. 8,816). No data are available on the male parent. The new cultivar was selected by me from the progeny of the stated parentage on or about November 1995. The first asexual reproduction of 'Tercedi' was accomplished when vegetative cuttings were taken on February 1996 in De Kwakel. The new cultivar is presently being propagated by cuttings and tissue culture. Horticultural examination of selected units initiated in 1997 has demonstrated that the combination of characteristics as herein disclosed for 'Tercedi' are firmly fixed and are retained through successive generations of asexual reproduction.

'Tercedi' has not been observed under all possible environmental conditions. The phenotype may vary significantly with variations in environment such as temperature, light intensity and day length. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Tercedi', which in combination distinguish this Gerbera from its parents and all other varieties of which I am aware:

1. Type: Semi-double.
2. Color of ray floret: Yellow.
3. Color of disc before opening of disc florets: Yellowish green, R.H.S. 144B.
4. Color of perianth lobe: Green R.H.S. 144A.
5. Diameter of flower head: 115 mm.

Of the many commercial cultivars known to me, there is no cultivar similar in comparison to 'Tercedi'.

BRIEF DESCRIPTION OF THE DRAWINGS

The accompanying photographic drawings show typical inflorescence and foliage characteristics of the new cultivar with the colors being shown as nearly true as is reasonably possible to attain in illustrations of this type.

The top photograph illustrates the flower head pictured across face.

The photograph at the bottom illustrates a typical leaf of the present invention.

BOTANICAL DESCRIPTION OF THE PLANT

*Botanical.—Gerbera jamesonii* cv. 'Tercedi'

In the following description, color references are made to The Royal Horticultural Society Colour Chart (R.H.S.). The color values were determined at 10:00 a.m. on Jan. 26, 1998 under artificial light at De Kwakel. The following traits have been repeatedly observed and are determined to be basic characteristics of 'Tercedi', which in combination distinguish this Gerbera as a new and distinct cultivar.

INFLORESCENCE

A. Flowerhead:

*Type.*—Semi-double.

*Diameter across face.*—Large (approx. 115 mm).

*Color* (*general tonality from a distance of* 3 *meters*) .—Yellow.

*Shape.*—Incurving funnel-shaped.

*Involucre.*—Height from point of attachment of involucre to top of flower head: medium (approx. 35 mm). Height: medium (approx. 20 mm). Diameter: large (approx. 50 mm). Number of bracts: medium (approx. 74). Longitudinal axis of inner rows: straight. Anthocyanin: absent. Pubescence: dense.

*Ray florets.*—Number: medium (68). Shape: obovate-narrow obovate. Longitudinal axis outer row: incurving. Longitudinal axis inner row: incurving. Longitudinal axis of ray female floret: incurving-straight.

*Outer ray floret.*—Cross section: flat. Length: long (approx. 55 mm). Width: medium (approx. 12 mm). Longitudinal folding: strong. Angle of apex: right angle. Shape of apex: pointed. Incisions of apex: 1–2. Depth of incision: shallow. Color (topside): R.H.S. 9A. Color (bottom side): R.H.S. 10B. Color distribution on inner side: uniform. Edge of different color: absent. Striation: absent. Claw spot: absent.

B. Disc florets:

*Disc diameter.*—Medium (approx. 25 mm).

*Color* (*immature, bottom*).—Yellow (90% at bottom, R.H.S. 5A).

*Color* (*immature, top*).—Purple (1 mm tip, R.H.S. 154A).

*Main color upperside corolla.*—Female flowers: yellow (R.H.S. 7A). Male flowers: yellow (R.H.S. 7A).

C. Reproductive organs:

*Style.*—Main color distal part: yellow green (R.H.S. 154B).

*Stigma.*—Main color: yellow (R.H.S. 4A).

*Anthers.*—Main color: dark yellow (R.H.S. 14B). Color of top relative to other parts is lighter, R.H.S. 14C for upper 1 mm. Longitudinal stripes are absent. Intensity of anthocyanin coloration is absent.

*Pappus.*—Main color: light green (R.H.S. 1D). Color of top relative to other parts is identical. Level of top relative to closed disc florets: same level.

*Fertility.*—Fertility as well as the seedsetting is good.

D. Peduncle:

*Length.*—Long (approx. 66 cm).

*Cross section.*—Round.

*Tendency to fasciation.*—Absent.

*Thickness.*—Medium.

*Strength.*—Medium.

*Pubescence.*—Medium.

*Color.*—Light green (R.H.S. 144A).

*Anthocyanin coloration.*—At base: absent or very weak (darker R.H.S. 153A). At top: absent.

*Involucral bracts.*—Absent.

PLANT

A. General appearance:

*Height.*—35 cm (exluding any flowers).

B. Foliage:

*Leaf blade.*—Length: medium (approx. 30 cm). Width: medium (approx. 16 cm). Thickness: medium. Blistering: medium. Pubescence: On upper side (midrib excluded): medium. Depth of cuts or incisions in leaf: Basal part: deep. Central part: deep. Distal part: medium. Color: Upper side of the leaf blade: light green (R.H.S. 138A) Bottom side of the leaf blade: R.H.S. 138B. Glossiness on upper side: weak. Angle of apex: acute. Shape of apex: rounded. Margin of lobes: irregular. Number of lobes: approx. 11 Extensions of margin: medium. Petiole length: medium (approx. 18 cm). Color of petiole: R.H.S. 145B. Petiole anthocyanin coloration: very weak (R.H.S. 187B).

C. Disease resistance: No special disease resistance.

I claim:

1. A new and distinct cultivar of Gerbera plant named 'Tercedi', substantially as herein shown and described, characterized particularly as to novelty by its characteristics enumerated above.

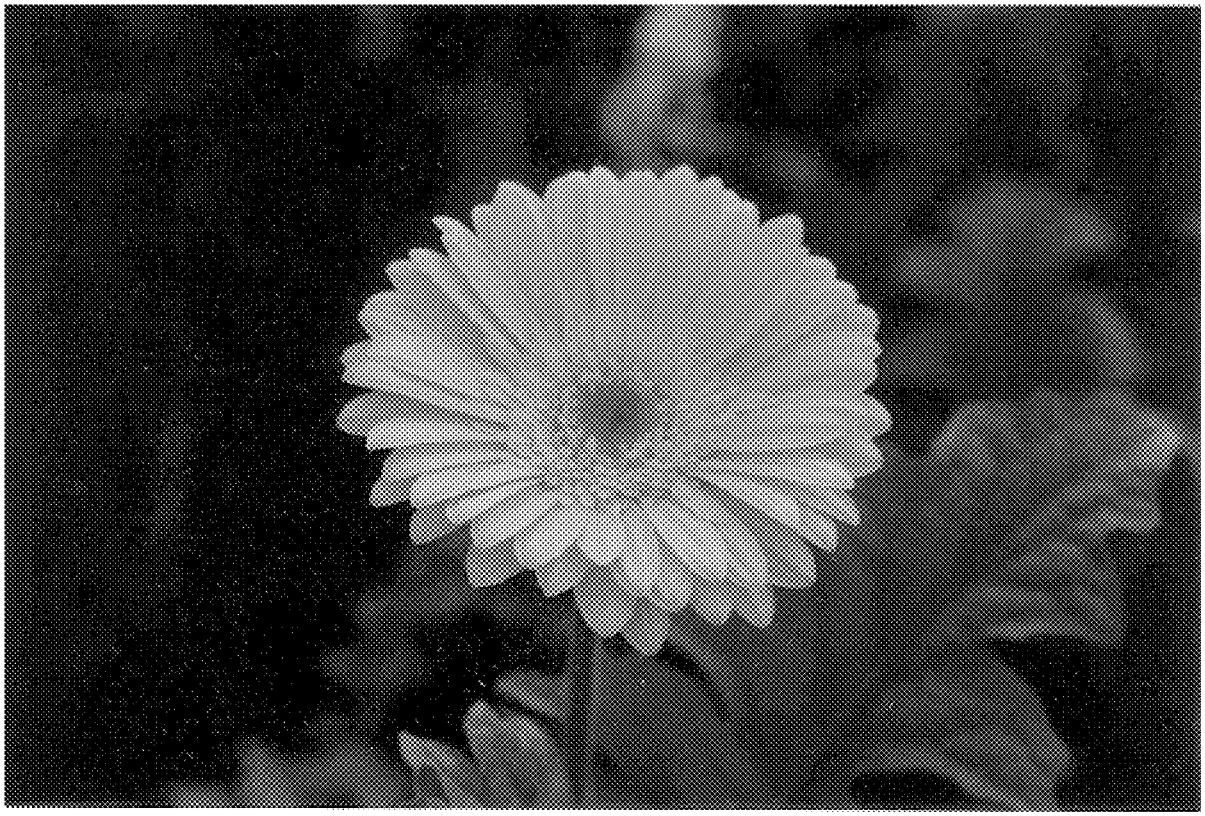
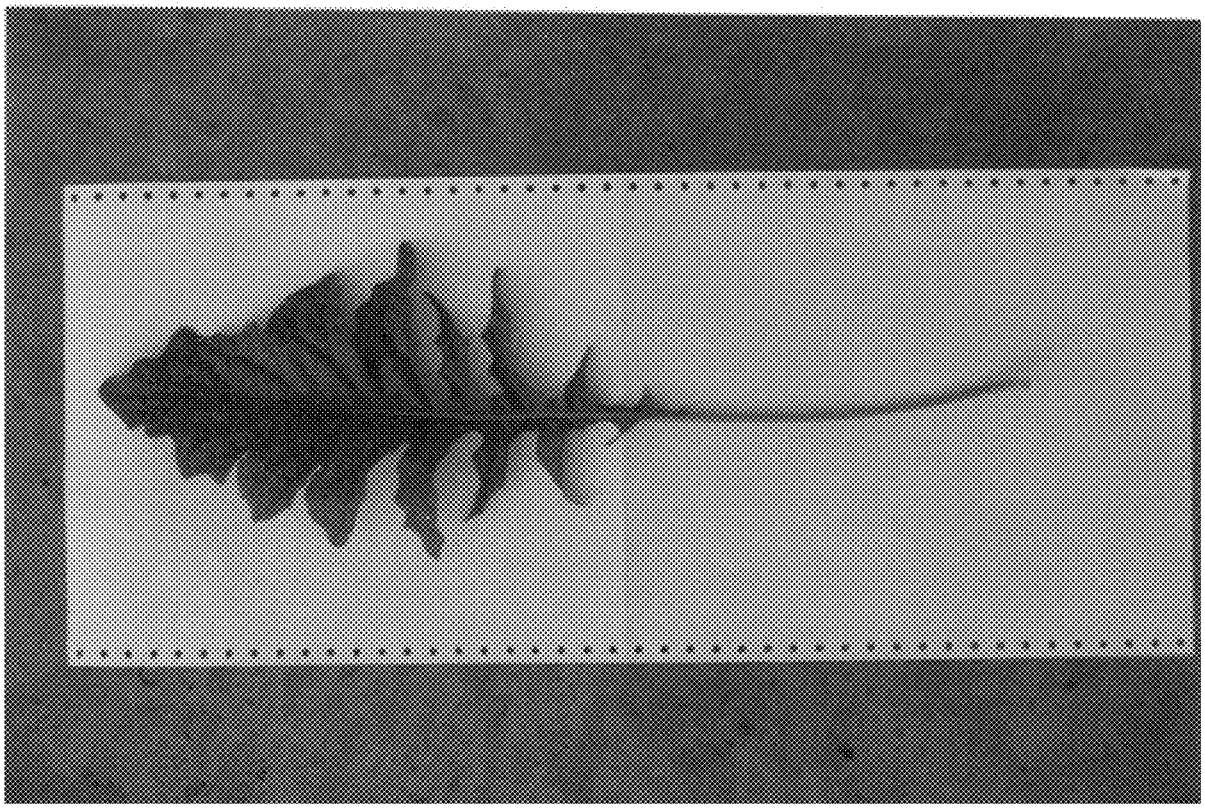

* * * * *